United States Patent [19]
Osorio et al.

[11] Patent Number: 6,106,841
[45] Date of Patent: Aug. 22, 2000

[54] DELIVERY METHOD FOR RECOMBINANT RACCOON POXVIRUS

[75] Inventors: Jorge E. Osorio, Mount Horeb, Wis.; Dan T. Stinchcomb, Fort Collins, Colo.

[73] Assignee: Heska Corporation, Fort Collins, Colo.

[21] Appl. No.: 09/018,798

[22] Filed: Feb. 4, 1998

[51] Int. Cl.$^7$ .................. A61K 39/12; A61K 39/275; A61K 39/205

[52] U.S. Cl. ................... 424/199.1; 424/224.1; 424/232.1

[58] Field of Search ............... 424/199.1, 93.2, 424/184.1, 204.1, 232.1, 224.1; 435/320.1

[56] References Cited

U.S. PATENT DOCUMENTS

| | | | |
|---|---|---|---|
| 5,266,313 | 11/1993 | Esposito et al. | 424/199.1 |
| 5,348,741 | 9/1994 | Esposito et al. | 424/199.1 |
| 5,607,846 | 3/1997 | Murphy et al. | 435/69.3 |
| 5,656,275 | 8/1997 | Wasmoen et al. | 424/199.1 |

FOREIGN PATENT DOCUMENTS

| | | |
|---|---|---|
| 0 652 287 A2 | 5/1995 | European Pat. Off. |
| WO 87/04624 | 8/1987 | WIPO . |
| WO 93/01284 | 1/1993 | WIPO . |
| WO 96/40268 | 12/1996 | WIPO . |

OTHER PUBLICATIONS

Hu et al. "raccoon poxvirus live recombinant feline panleukopenia virus VP2 and rabies virus glycoprotein bivalent vaccine". Vaccine. vol. 15, No. 12/13, pp. 1466–1472, 1997.

Hu et al. "raccoon poxvirus feline panleukopenia virus VP2 recombinant protects cats against FPV challenge". Virology. vol. 218, 248–252, 1996.

Ramshaw et al. "expression of cytokines by recombinant vaccinia viruses: a model for studying cytokines in virus infections in vivo". Immunological Reviews. vol. 127, pp. 157–182, 1992.

Esposito et al, Advances in Veterinary Science and Comparative Medicine 33:195–247, 1989.

Hall et al, The Lancet, Jan. 10, 1987, p. 111.

O'Connor et al, British Journal of Opthamology 74:245–246, 1990.

Ngichare, Dissertation Abstracts International 53 (8):3936–B, 1993.

Esposito et al., 1988, *Virology* 165, pp. 313–316.

Esposito et al., 1992, *Vaccines* 92, pp. 321–329.

Herman, 1964, Bacteriol. Proc. 64th Annual Meeting of the Am. Soc. Microbiol., p. 117.

Thomas et al., 1975, *Archives of Virology* 49, pp. 217–227.

Lutze–Wallace et al., 1995, *Virus Genes* 10:1, pp. 81–84.

Scott, F. W., 1988, 69th Conf. Res. Workers Anim. Dis., Abstract 60.

Database WPI, Week 9711, Derwent Publications, Ltd., XP002107225, Jan. 7, 1997.

Database WPI, Week 9135, Derwent Publications, Ltd., XP002107226, Jul. 23, 1991.

DeMartini et al., 1993, *Arch Virol*, 133, pp. 211–222.

*Primary Examiner*—Mary E. Mosher
*Attorney, Agent, or Firm*—Heska Corporation

[57] ABSTRACT

The present invention relates to a novel method to immunize an animal against a heterologous antigen. The method includes the step of administering to the animal, by an intranasal route, a conjunctival route, or a combination thereof, a composition comprising a recombinant raccoon poxvirus having a nucleic acid molecule encoding such a heterologous antigen. Animals to be immunized include those that are susceptible to such routes of recombinant raccoon poxvirus administration. Preferred animals to immunize include felids. Preferably, any immune response generated by the animal against viral antigens of the recombinant raccoon poxvirus is sufficiently small so as to not prevent the animal from eliciting an immune response to a heterologous antigen encoded by a recombinant raccoon poxvirus subsequently administered to the animal.

17 Claims, No Drawings

DELIVERY METHOD FOR RECOMBINANT RACCOON POXVIRUS

FIELD OF THE INVENTION

The present invention relates to a novel method to deliver recombinant raccoon poxviruses to mammals in order to elicit immune responses against heterologous antigens encoded by the recombinant raccoon poxviruses. In particular, the present invention relates to the intranasal and/or conjunctival administration of recombinant raccoon poxviruses to felids.

BACKGROUND OF THE INVENTION

Raccoon poxvirus is an indigenous orthopoxvirus (family: Poxviridae) that infects North American raccoons. The virus is an enveloped, double stranded DNA virus (Family-Poxviridae; Subfamily-Chordapoxviridae; Genus-Orthopoxvirus), first isolated from the upper respiratory tract tissue of 2 of 92 apparently healthy raccoons during a survey of wildlife at Aberdeen Proving Grounds, Maryland; see, Herman, 1964, Bacteriol. Proc. $64^{th}$ Ann. Meeting of the Am. Soc. Microbiol., p. 117.

For several years, recombinant raccoon poxviruses have been used as delivery systems for heterologous (i.e., foreign) nucleic acid molecules. See, for example, Esposito et al., 1988, Virology 165, 313–316; Esposito et al., 1992, In: Vaccines 92, Cold Spring Harbor Laboratory, pp. 321–329; U.S. Pat. No. 5,266,313, dated Nov. 30, 1993, by Esposito et al.; and U.S. Pat. No. 5,348,741, dated Sep. 20, 1994, by Esposito et al., each of which is incorporated herein by reference in its entirety. Heterologous nucleic acid molecules encoding antigens have been inserted into the thymidine kinase (TK) gene by homologous recombination; see, for example, Esposito et al., 1988, ibid. Such an insertion inactivates the TK gene, markedly reducing raccoon poxvirus virulence. Previous studies have studied the efficacy of oral or parentally delivered recombinant raccoon poxviruses in a wide range of animals including foxes, bobcats, rabbits, domestic cats, piglets, sheep and non-human primates; see, for example, Esposito et al., 1992, ibid.

Although recombinant raccoon poxviruses have been delivered using subcutaneous, intramuscular, and oral routes of administration, there are drawbacks to each of these administration routes. Intramuscular and subcutaneous forms of vaccine delivery have been correlated with a sporadic incidence of injection-site sarcomas. Furthermore, intramuscular or subcutaneous delivery of recombinant raccoon poxviruses leads to the production of high titers of antibodies against the raccoon poxvirus itself. Such antibody production interferes with the ability to use raccoon poxvirus as a delivery system for subsequent immunizations. In addition, booster administrations are typically required to obtain an efficacious immune response. Delivery of recombinant raccoon poxviruses by the oral route also has several disadvantages: This route of immunization requires administration of high titers of virus (typically more than $10^8$ plaque forming units (pfu)) as well as the need for several immunizations in order to obtain an effective antibody response.

There remains a need for a viral vector-based delivery system that can elicit an efficacious and safe immune response, and in particular a mucosal immune response. Such a delivery system preferably would be administered mucosally, would elicit an efficacious immune response against the heterologous antigen encoded by the recombinant virus without requiring a booster dose, and would elicit a sufficiently low response against viral antigens so as to allow for subsequent administration of one or more additional recombinant virus(es) leading to an efficacious immune response against the additional heterologous antigen(s) encoded therein.

SUMMARY OF THE INVENTION

The present invention includes a method to immunize an animal against a heterologous antigen. The method includes the step of administering to the animal, by an intranasal route, a conjunctival route, or a combination thereof, a composition comprising a recombinant raccoon poxvirus having a nucleic acid molecule encoding such a heterologous antigen. Animals to be immunized include those that are susceptible to such routes of recombinant raccoon poxvirus administration. Preferred animals to immunize include felids. Preferably, an immune response generated by the animal against viral antigens of the recombinant raccoon poxvirus does not prevent the animal from eliciting an immune response to a heterologous antigen encoded by a recombinant raccoon poxvirus subsequently administered to the animal.

DETAILED DESCRIPTION OF THE INVENTION

The present invention relates to a novel method to deliver recombinant raccoon poxviruses that addresses the needs outlined above, namely the need for a safer and more efficacious delivery system. The novel method disclosed herein involves administration of a recombinant raccoon poxvirus by an intranasal route, a conjunctival route, or a combination thereof, to effect an immune response in animals susceptible to such a route of administration. The inventors believe no one to date has reported intranasal and/or conjunctival administration of a recombinant raccoon poxvirus to obtain an immune response. This novel method has a number of advantages including the development of high levels of circulating antibodies against a heterologous antigen encoded by the recombinant raccoon poxvirus without the need for large dose sizes or multiple administrations. This method furthermore leads to the generation of only a low serological response against the raccoon poxvirus itself. The mechanism by which these routes of administration lead to a higher immune response against a heterologous antigen is not clear. While not being bound by theory, the finding of native raccoon poxvirus in the upper respiratory tract suggests the nasal cavity as the virus' natural route of entry. Thus, it is possible that the routes disclosed herein might simulate the natural pathway of raccoon poxvirus infection.

The present invention includes a method to immunize an animal against a heterologous antigen. The method includes the step of administering to the animal, by an intranasal route, a conjunctival route, or a combination thereof, a composition comprising a recombinant raccoon poxvirus having a nucleic acid molecule encoding such a heterologous antigen. Animals to be immunized include those that are susceptible to such routes of recombinant raccoon poxvirus administration (i.e., animals that are able to generate an immune response against a heterologous antigen encoded by a recombinant raccoon poxvirus administered by an intranasal route, by a conjunctival route, or by a combination thereof). Preferred animals to immunize include felids. As used herein, a felid, or a cat, refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat to immunize is a domestic cat.

It is to be noted that the term "a" or "an" entity refers to one or more of that entity; for example, an antigen refers to one or more antigens, or to at least one antigen. As such, the terms "a" (or "an"), "one or more" and "at least one" can be used interchangeably herein. It is also to be noted that the terms "comprising", "including", and "having" can be used interchangeably. Furthermore, an administration route "selected from the group consisting of" refers to one or more of the routes in that group, including combinations thereof.

As used herein, the terms immunize, immunized and immunization refer to the ability to elicit an immune response in an animal. An immune response can be humoral or cell-mediated, or a combination thereof. Methods to measure an immune response are known to those skilled in the art; examples of some of such methods are disclosed herein. In one embodiment, a preferred immune response is a mucosal immune response. In a preferred embodiment an immunized animal is protected from disease caused by the agent against which the animal is being immunized. For example, in a preferred embodiment, immunization of an animal with a recombinant raccoon poxvirus expressing rabies glycoprotein G will protect that animal from rabies. Such an animal preferably displays (i.e., has) a protective antibody titer. Particularly preferred are high rabies antibody titers, as measured by rapid focus fluorescent inhibition test (RFFIT; see examples), of at least about 1:1500. It is to be noted that such a number is substantially higher than the amount required to protect an animal from rabies (e.g., a RFFIT titer of at least about 1:5 is considered to be protective).

Intranasal and conjunctival methods to administer compositions to animals in order to effect immunization are known to those skilled in the art, including suitable formulations, doses, dose schedules, and methodologies. As used herein, administration of a recombinant raccoon poxvirus by an intranasal route refers to applying such a poxvirus to the nose, for example by drops or spray delivered into one or both nostrils. As used herein, administration of a recombinant raccoon poxvirus by a conjunctival route refers to applying such a poxvirus to one or both eyes, for example, by drops or spray to the conjunctival mucosa of one or both eyes.

A preferred dose of recombinant raccoon poxvirus to administer to a cat is at least about $1\times10^8$ pfu, with at least about $1\times10^7$ pfu being more preferred and at least about $1\times10^6$ pfu being even more preferred. Particularly preferred is a dose ranging from about $1\times10^6$ pfu to about $1\times10^8$ pfu. Such doses are advantageous in that they are lower than is often required for administering recombinant raccoon poxvirus by other routes.

An advantage of administering recombinant raccoon poxviruses intranasally and/or conjunctively as disclosed herein is that while booster doses can be administered they are not necessary to immunize the animal in an effective manner. For example, a single intranasal and/or conjunctival administration of a recombinant raccoon poxvirus expressing rabies glycoprotein G is sufficient to elicit the production of a titer of rabies virus neutralizing antibodies known to be sufficient to protect an animal against rabies disease.

A recombinant raccoon poxvirus of the present invention can be formulated in an excipient that the animal to be treated can tolerate. As such, the present invention includes administration of a composition comprising a recombinant raccoon poxvirus, wherein the composition further comprises an excipient. Examples of such excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline can be added prior to administration.

In one embodiment of the present invention, the recombinant raccoon poxvirus can also include an adjuvant and/or a carrier. One advantage of a recombinant raccoon poxvirus is that adjuvants and carriers are not required to produce an efficacious vaccine, and in some cases, the advantages of the poxviruses of the present invention would be precluded by the use of some adjuvants. However, it should be noted that use of adjuvants or carriers is not precluded by the present invention. Adjuvants are typically substances that generally enhance the immune response of an animal to a specific antigen. Suitable adjuvants include, but are not limited to, other bacterial cell wall components; aluminum-based salts; calcium-based salts; silica; polynucleotides; toxoids; serum proteins; other viral coat proteins; other bacterial-derived preparations; block copolymer adjuvants, such as TITERMAX® adjuvant (CYTRX®, Inc. Norcross Ga.); RIBI adjuvants (available from Ribi ImmunoChem Research, Inc., Hamilton Mont.); and saponins and their derivatives such as QUIL A (available from Superfos Biosector A/S Denmark). Carriers are typically compounds that increase the half-life of a therapeutic composition in the treated animal. Suitable carriers include, but are not limited to, polymeric controlled release formulations, biodegradable implants, liposomes, bacteria, viruses, oils, esters, and glycols.

Preferably, administration of a recombinant raccoon poxvirus in accordance with the present invention does not interfere with one or more subsequent administrations of recombinant raccoon poxviruses. That is, preferably any immune response generated by an animal against viral antigens of the recombinant raccoon poxvirus (i.e., anti-raccoon poxvirus antibodies) is sufficiently small as to not prevent (or substantially interfere with) the animal being able to elicit an immune response to a heterologous antigen encoded by a recombinant raccoon poxvirus subsequently administered to that animal. The inventors have discovered that although intranasal and/or conjunctival administration of a recombinant raccoon poxviruses elicits a high titer of antibodies against the heterologous antigen(s) encoded by the recombinant raccoon poxvirus, only very low titers of antibodies against the poxvirus itself are generated, allowing for successful subsequent recombinant raccoon poxvirus administrations.

As used herein, a recombinant raccoon poxvirus is a raccoon poxvirus that comprises (i.e., has or includes) a genome that has been genetically engineered (i.e., subjected to recombinant nucleic acid (i.e., DNA or RNA) techniques, such as those disclosed in Sambrook et al., 1989, *Molecular Cloning: A Laboratory Manual,* Cold Spring Harbor Labs Press; Sambrook et al., ibid., is incorporated by reference herein in its entirety) to differ from the genome of a natural raccoon poxvirus isolate. Such a genetically engineered genome is referred to herein as a recombinant raccoon poxvirus genome and is described in more detail below.

A recombinant raccoon poxvirus of the present invention includes not only a recombinant raccoon poxvirus genome but also an envelope and core in which the genome is packaged. The viral envelope and core are preferably a raccoon poxvirus envelope and a raccoon poxvirus core, encoded at least in part by raccoon poxvirus genes, thereby imparting to the recombinant raccoon poxvirus the host range of a natural raccoon poxvirus isolate. It is to be noted, however, that the present invention also includes recombinant raccoon poxviruses having envelopes and/or cores that have been modified to, for example, alter (e.g., broaden, narrow, or completely change) the host range of the recombinant raccoon poxvirus genome. Such modifications can be accomplished by one skilled in the art by, for example, modifying raccoon poxvirus envelope and/or core genes and/or replacing such genes with those of another virus. Altered genes can be located on the raccoon poxvirus genome itself and/or in the genome of the cell in which the recombinant virus is produced.

A recombinant raccoon poxvirus genome of the present invention is a raccoon poxvirus genome in which nucleotides have been deleted, inserted, substituted or inverted using recombinant techniques known to those skilled in the art such that the recombinant raccoon poxvirus genome is no longer the same as a natural genome. A recombinant raccoon poxvirus genome of the present invention includes a (i.e., one or more) heterologous nucleic acid molecule. As used herein, a heterologous nucleic acid molecule is a nucleic acid molecule isolated from a source other than raccoon poxvirus. In a preferred embodiment, a heterologous nucleic acid molecule of the present invention encodes a protein, such as a heterologous antigen, that is, a non-raccoon poxvirus antigen.

A heterologous nucleic acid molecule of the present invention is operatively linked to a transcription control region, meaning that the heterologous nucleic acid molecule is expressed as an RNA and/or protein by the recombinant viral genome upon infection into a cell. The transcription control region can be endogenous to the genome or the heterologous nucleic acid molecule can be operatively linked to an exogenous transcription control region to form a recombinant molecule. Such a recombinant molecule can be introduced into the genome by methods known to those skilled in the art, for example by homologous recombination.

A suitable transcription control sequence is any sequence that allows for transcription of a heterologous nucleic acid molecule of the present invention. Examples include, but are not limited to, poxvirus promoters such as p11, p7.5, and synthetic promoters, as well as other viral promoters such as CMV promoters.

A suitable location for a heterologous nucleic acid molecule or recombinant molecule of the present invention is in an essential region, a non-essential region, or an intergenic region of the raccoon poxvirus genome. Examples include, but are not limited to, a thymidine kinase gene, a hemagglutinin gene, a serpin gene, a cytokine receptor gene, and an interferon receptor gene.

A suitable heterologous antigen is any antigen that effects an immune response, and as such includes allergens. Preferred antigens are those that elicit an immune response that protects an animal from disease. Examples of such antigens include, but are not limited to, a protozoan parasite antigen, a helminth parasite antigen, an ectoparasite antigen, a fungal antigen, a bacterial antigen, and a viral antigen. Examples of viral antigens include, but are not limited to, antigens from adenoviruses, caliciviruses, coronaviruses, distemper viruses, hepatitis viruses, herpesviruses, immunodeficiency viruses, infectious peritonitis viruses, leukemia viruses, oncogenic viruses, papilloma viruses, parainfluenza viruses, parvoviruses, rabies viruses, and reoviruses, as well as other cancer-causing or cancer-related viruses. Examples of bacterial antigens include, but are not limited to, antigens from Actinomyces, Bacillus, Bacteroides, Bordetella, Bartonella, Borrelia, Brucella, Campylobacter, Capnocytophaga, Clostridium, Corynebacterium, Coxiella, Dermatophilus, Enterococcus, Ehrlichia, Escherichia, Francisella, Fusobacterium, Haemobartonella, Helicobacter, Klebsiella, L-form bacteria, Leptospira, Listeria, Mycobacteria, Mycoplasma, Neorickettsia, Nocardia, Pasteurella, Peptococcus, Peptostreptococcus, Proteus, Pseudomonas, Rickettsia, Rochalimaea, Salmonella, Shigella, Staphylococcus, Streptococcus, and Yersinia. Examples of fungal antigens include, but are not limited to, antigens from Absidia, Acremonium, Alternaria, Aspergillus, Basidiobolus, Bipolaris, Blastomyces, Candida, Chlamydia, Coccidioides, Conidiobolus, Cryptococcus, Curvalaria, Epidermophyton, Exophiala, Geotrichum, Histoplasma, Madurella, Malassezia, Microsporum, Moniliella, Mortierella, Mucor, Paecilomyces, Penicillium, Phialemonium, Phialophora, Prototheca, Pseudallescheria, Pseudomicrodochium, Pythium, Rhinosporidium, Rhizopus, Scolecobasidium, Sporothrix, Stemphylium, Trichophyton, Trichosporon, and Xylohypha. Example of protozoan and helminth parasite antigens include, but are not limited to, antigens from Babesia, Balantidium, Besnoitia, Cryptosporidium, Eimeria, Encephalitozoon, Entamoeba, Giardia, Hammondia, Hepatozoon, Isospora, Leishmania, Microsporidia, Neospora, Nosema, Pentatrichomonas, Plasmodium, Pneumocystis, Sarcocystis, Schistosoma, Theileria, Toxoplasma, and Trypanosoma, Acanthocheilonema, Aelurostrongylus, Ancylostoma, Angiostrongylus, Ascaris, Brugia, Bunostomum, Capillaria, Chabertia, Cooperia, Crenosoma, Dictyocaulus, Dioctophyme, Dipetalonema, Diphyllobothrium, Diplydium, Dirofilaria, Dracunculus, Enterobius, Filaroides, Haemonchus, Lagochilascaris, Loa, Mansonella, Muellerius, Nanophyetus, Necator, Nematodirus, Oesophagostomum, Onchocerca, Opisthorchis, Ostertagia, Parafilaria, Paragonimus, Parascaris, Physaloptera, Protostrongylus, Setaria, Spirocerca, Spirometra, Stephanofilaria, Strongyloides, Strongylus, Thelazia, Toxascaris, Toxocara, Trichinella, Trichostrongylus, Trichuris. Uncinaria, and Wuchereria. Examples of ectoparasite antigens include, but are not limited to, antigens (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Preferred antigens include, but are not limited to, a calicivirus antigen, a coronavirus antigen, a herpesvirus antigen, an immunodeficiency virus antigen, an infectious peritonitis virus antigen, a leukemia virus antigen, a panleukopenia virus antigen, a parvovirus antigen, a rabies virus antigen, a Bartonella antigen, a Yersinia antigen, a Dirofilaria antigen, a Toxoplasma antigen, a tumor antigen, a flea antigen, a flea allergen, a midge antigen, a midge allergen, a mite antigen, and a mite allergen. Particularly preferred antigens include a rabies virus glycoprotein G antigen; heartworm PLA2, P39, P4, P22U, Gp29, astacin, cysteine protease, macrophage migration inhibitory factor, venom allergen, TPX-1, TPX-2, transglutaminase, ankyrin, and asparaginase antigens; flea serine protease, cysteine protease, aminopeptidase, serpin, carboxylesterase, juvenile hormone esterase, and epoxide hydrolase antigens; flea salivary antigens; Yersinia F1 and V antigens; and *Toxoplasma gondii* antigens such as those disclosed in U.S. patent application Ser. No. 08/994,825, filed Dec. 19, 1997, by Milhausen et al., entitled "*Toxoplasma gondii* Proteins, Nucleic Acid Molecules, and Uses Thereof", which is incorporated by reference herein in its entirety.

One embodiment of the present invention is a recombinant raccoon poxvirus that also comprises a nucleic acid molecule encoding an immunomodulator. Suitable immunomodulators include compounds that enhance certain immune responses as well as compounds that suppress certain immune responses. Compounds that enhance the immune response include compounds that preferentially enhance humoral immunity as well as compounds that preferentially enhance cell-mediated immunity. Suitable compounds can be selected depending on the desired outcome. Suitable immunomodulators include, but are not limited to, cytokines, chemokines, superantigens, and other immunomodulators as well as compounds that induce the production of cytokines, chemokines and other immunomodulators. Examples of such compounds include, but are not limited to, granulocyte macrophage colony stimulating factor (GM-CSF), granulocyte colony stimulating factor (G-CSF), macrophage colony stimulating factor (M-CSF), colony stimulating factor (CSF), erythropoietin (EPO), interleukin 2 (IL-2), interleukin-3 (IL-3), interleukin 4 (IL-4), interleukin 5 (IL-5), interleukin 6 (IL-6), interleukin 7 (IL-7), interleukin 8 (IL-8), interleukin 10 (IL-10), interleukin 12 (IL-12), interferon gamma, interferon gamma inducing factor I (IGIF), transforming growth factor beta (TGF-β), RANTES (regulated upon activation, normal T-cell expressed and presumably secreted), macrophage inflammatory proteins (e.g., MIP-1 alpha and MIP-1 beta), and Leishmania elongation initiating factor (LEIF).

A suitable recombinant raccoon poxvirus includes one or more of any of the aforementioned heterologous nucleic acid molecules. A particularly preferred recombinant raccoon poxvirus expresses a rabies glycoprotein G protein, such as RCNV/rabies gG (also referred to herein as RCN/G), which is described in the Examples. Other examples of preferred recombinant raccoon poxviruses can be found in PCT Patent Publication WO 97/18229, published May 22, 1997, by Tripp et al., entitled "Parasitic Helminth Macrophage Migration Inhibitory Factor Proteins, Nucleic Acid Molecules, and Uses Thereof"; and in PCT Application Serial No. PCT/US97/22617, filed Dec. 4, 1997, by Haanes et al., entitled "Recombinant Plague Vaccine". Each of these two references is incorporated by reference herein in its entirety. Additional preferred recombinant raccoon poxviruses include RCNV/PLA2 poxviruses, which are similar to the recombinant raccoon poxviruses disclosed in the two references cited immediately above, except that the heterologous nucleic acid molecules in RCNV/PLA2 poxviruses are at least one of the nucleic acid molecules encoding a heartworm PLA2 antigen as disclosed in U.S. patent application Ser. No. 08/482,304, filed Jun. 7, 1995, by Grieve et al., entitled "Novel Parasitic Helminth PLA2 Proteins and Nucleic Acid Molecules". U.S. patent application Ser. No. 08/482,304 is incorporated by reference herein in its entirety.

A suitable composition for administering to animals in accordance with the present invention can include one or more recombinant raccoon poxviruses, each including one or more heterologous nucleic acid molecules, as disclosed herein. As such, a composition of the present invention can be multivalent—either delivering one or more antigens derived from a single source or antigens from multiple sources, such as those disclosed herein.

Heterologous nucleic acid molecules, recombinant molecules, recombinant raccoon poxvirus genomes, recombinant raccoon poxviruses and compositions of the present invention can be produced by methods known to those skilled in the art.

The following examples are provided for the purposes of illustration and are not intended to limit the scope of the present invention.

EXAMPLES

Example 1

This Example demonstrates that intranasal and/or conjunctival administration of a recombinant raccoon poxvirus expressing the rabies glycoprotein G (gG) antigen elicits an immune response against the rabies antigen that is superior to that elicited by oral administration of the same poxvirus.

Recombinant raccoon poxvirus RCNV/rabies gG, also denoted RCN/G, available from Dr. Joseph Esposito, Centers for Disease Control, Atlanta, Ga. (see also Esposito et al., 1988, ibid.), includes, within the thymidine kinase gene of the virus, a heterologous nucleic acid molecule encoding a rabies glycoprotein G protein operatively linked to a poxvirus p11 promoter. For the following studies, RCN/G was grown and amplified in Vero cells using procedures described in the art. Vaccine doses were prepared from a stock RCN/G virus titering $1.5 \times 10^9$ pfu, using minimal essential medium (MEM, Gibco BRL) as a diluent. Final vaccine doses also contained 20% glycerol. The vaccine volumes used were 100 microliters per nostril for intranasal delivery, 35 microliters per eye for conjunctival delivery, and 1 milliliter for oral delivery.

In order to characterize and compare immune responses in cats exposed to RCN/G by oral, intranasal, conjunctival, or intranasal and conjunctival routes of administration, the following experiment was performed. Four groups of four, 6-month old cats were housed in individual cages. Group 1 was exposed to $4 \times 10^7$ pfu of RCN/G by an intranasal route (IN) of administration. Group 2 was exposed to $1 \times 10^7$ pfu of RCN/G by a conjunctival route (CO) of administration. Group 3 was exposed to $5 \times 10^7$ pfu of RCN/G by intranasal and conjunctival routes (IN/CO) of administration. Group 4 was exposed to $1 \times 10^8$ pfu of RCN/G by an oral route of administration. Blood samples were collected from all animals at 0, 10, 20, and 30 days post-inoculation (PI). The samples were tested for rabies virus neutralizing antibodies (Rabies Ab) by the rapid focus fluorescent inhibition test (RFFIT), conducted at Kansas State University. The samples were also tested for neutralizing antibodies against raccoon poxvirus (RCNV Ab) by the serum neutralization test (SNT). Results, expressed in terms of antibody titers (Ab Titers), derived in a manner known to those skilled in the art, are summarized in Table 1.

TABLE 1

| Animal ID | Route | Dose | Rabies Ab Titers (RFFIT) Day 0 | Day 30 | RCNV Ab Titers (SNT) Day 0 | Day 30 |
|---|---|---|---|---|---|---|
| QWO4 | IN | $4 \times 10^7$ | <1:5 | 1:1100 | <1:5 | 1:125 |
| QUZ3 | IN | $4 \times 10^7$ | <1:5 | 1:2400 | <1:5 | 1:125 |
| QWO3 | IN | $4 \times 10^7$ | <1:5 | 1:3125 | <1:5 | 1:25 |
| QUX3 | IN | $4 \times 10^7$ | <1:5 | >1:7000 | <1:5 | 1:25 |
| QWK2 | CO | $1 \times 10^7$ | <1:5 | 1:5400 | <1:5 | 1:25 |
| QWF3 | CO | $1 \times 10^7$ | <1:5 | 1:1300 | <1:5 | 1:25 |
| BWR3 | CO | $1 \times 10^7$ | <1:5 | 1:1800 | <1:5 | 1:25 |
| QWL1 | CO | $1 \times 10^7$ | <1:5 | 1:50 | <1:5 | 1:25 |
| QUZ2 | IN/CO | $5 \times 10^7$ | <1:5 | >1:7000 | <1:5 | 1:125 |
| QUL1 | IN/CO | $5 \times 10^7$ | <1:5 | <1:5 | <1:5 | <1:5 |
| QUQ1 | IN/CO | $5 \times 10^7$ | <1:5 | >1:6300 | <1:5 | 1:125 |
| QUN1 | IN/CO | $5 \times 10^7$ | <1:5 | >1:6000 | <1:5 | 1:25 |
| QWD2 | Oral | $1 \times 10^8$ | <1:5 | 1:270 | <1:5 | 1:25 |
| QUD1 | Oral | $1 \times 10^8$ | <1:5 | <1:5 | <1:5 | <1:5 |
| QUK1 | Oral | $1 \times 10^8$ | <1:5 | 1:1000 | <1:5 | 1:125 |
| QVW2 | Oral | $1 \times 10^8$ | <1:5 | 1:1100 | <1:5 | 1:125 |

Analysis of these results indicates that intranasal, conjunctival, and intranasal/conjunctival administration of a single dose of RCN/G in general elicits a higher antibody titer against rabies glycoprotein G than does oral administration of a single higher dose of the same vaccine. The antibody titer is significantly higher than that required to protect cats from rabies. Furthermore, titers against raccoon poxvirus antigens are low.

Example 2

This Example demonstrates the ability to obtain high antibody titers against rabies glycoprotein G when a recombinant raccoon poxvirus expressing glycoprotein G was administered to cats intranasally and/or conjunctivally.

In order to further characterize immune responses in cats exposed to RCN/G (virus produced as described in Example 1) by intranasal, conjunctival, or intranasal and conjunctival routes of administration, the following experiment was performed. Three groups of four, 6-month old cats were housed in individual cages. Group 1 was exposed to $1 \times 10^8$ pfu of RCN/G by an intranasal route (IN) of administration. Group 2 was exposed to $1 \times 10^8$ pfu of RCN/G by a conjunctival route (CO) of administration. Group 3 was exposed to $1 \times 10^8$ pfu of RCN/G by combined intranasal and conjunctival routes (IN/CO) of administration. Blood samples were collected from all animals at 0, 10, 20, and 30 days post-inoculation (PI). The samples were tested for rabies virus neutralizing antibodies (Rabies Ab) and for neutralizing antibodies against raccoon poxvirus (RCNV Ab) as described in Example 1. Results, expressed in terms of antibody titers (Ab Titers), are summarized in Table 2.

TABLE 2

| Animal ID | Route | Dose | Rabies Ab Titers (RFFIT) Day 0 | Day 30 | RCNV Ab Titers (SNT) Day 0 | Day 30 |
|---|---|---|---|---|---|---|
| BXI2 | IN | $1 \times 10^8$ | <1:5 | 1:1400 | <1:5 | 1:25 |
| 3591 | IN | $1 \times 10^8$ | <1:5 | 1:1600 | <1:5 | 1:125 |
| BWG2 | IN | $1 \times 10^8$ | <1:5 | 1:1400 | <1:5 | 1:3125 |
| 3592 | IN | $1 \times 10^8$ | <1:5 | >1:7000 | <1:5 | 1:25 |
| BVX5 | CO | $1 \times 10^8$ | <1:5 | 1:1100 | <1:5 | 1:125 |
| BWO5 | CO | $1 \times 10^8$ | <1:5 | 1:1300 | <1:5 | 1:125 |
| BWG3 | CO | $1 \times 10^8$ | <1:5 | 1:1400 | <1:5 | 1:5 |
| G262 | CO | $1 \times 10^8$ | <1:5 | 1:1800 | <1:5 | 1:125 |
| G387 | IN/CO | $1 \times 10^7$ | <1:5 | 1:5400 | <1:5 | 1:625 |
| 3590 | IN/CO | $1 \times 10^8$ | <1:5 | 1:6000 | <1:5 | 1:25 |
| 3589 | IN/CO | $1 \times 10^8$ | <1:5 | 1:1400 | <1:5 | 1:25 |
| G389 | IN/CO | $1 \times 10^8$ | <1:5 | 1:6000 | <1:5 | 1:3125 |

In this study, at a single dose of $1 \times 10^8$ pfu of RCN/G, all cats seroconverted to produce protective titers of anti-rabies glycoprotein G antibodies.

Example 3

This Example demonstrates that of cats given a single oral dose of a recombinant raccoon poxvirus expressing glycoprotein G, only about half showed rabies antibody titers considered to be protective against rabies.

Each of 16 cats was exposed to $1 \times 10^8$ pfu of RCN/G (produced as described in Example 1) by an oral route of administration. Blood samples were collected from all animals at 0 and 21 days post-inoculation (PI). The samples were tested for rabies virus neutralizing antibodies (Rabies Ab) by assays conducted by the Rabies Lab, New York State Department of Health, Albany, N.Y. Results, expressed in terms of IU/ml antibody titers (Ab Titers), are summarized in Table 3. (It is to be noted that a RFFIT of 1:16 is equivalent to 0.5 IU/ml.)

TABLE 3

| Animal ID | Rabies Ab Titer (IU/ml) Day 0 PI | Rabies Ab Titer (IU/ml) Day 21 PI |
|---|---|---|
| AIB3 | <.125 | <.125 |
| AIP1 | <.125 | ≧16 |
| AIL1 | <.125 | .125 |
| AIH1 | <.125 | <.125 |
| AIL3 | <.125 | <.125 |
| AIB2 | <.125 | <.125 |
| AIE1 | <.125 | <.125 |
| AHT3 | <.125 | 8 |
| AIQ4 | <.125 | 2 |
| AIO2 | <.125 | <.125 |
| AIJ1 | <.125 | .125 |
| AHZ1 | <.125 | 1 |
| AIR1 | <.125 | 2 |
| AIH2 | <.125 | 8 |
| AIQ3 | <.125 | 4 |
| AHR2 | <.125 | <.125 |

Analysis of these results indicates that only 9 of the 16 cats administered a single oral dose of a recombinant raccoon poxvirus expressing rabies glycoprotein G developed a protective immune response against rabies glycoprotein G. Using this assay, a rabies antibody titer of at least about 0.125 IU/ml is required to protect an animal from rabies.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to immunize a felid against a heterologous antigen, said method comprising administering to said felid a composition comprising a recombinant raccoon poxvirus having a nucleic acid molecule encoding said heterologous antigen, said administering comprising a conjunctival route.

2. A method to immunize a felid against a heterologous antigen, said method comprising administering to said felid a composition comprising a recombinant raccoon poxvirus having a nucleic acid molecule encoding said heterologous antigen, said administering comprising intranasal and conjunctival routes.

3. A method to immunize a felid against a heterologous antigen, said method comprising administering to said felid a composition comprising from about $10^7$ to about $10^8$ plaque forming units of a recombinant raccoon poxvirus having a nucleic acid molecule encoding said heterologous antigen, said administering being by a route selected from the group consisting of an intranasal route and a conjunctival route, wherein a single administration provides an immune response against said heterologous antigen.

4. The method of claim 3, wherein said felid displays an antibody response against said heterologous antigen at about thirty days post administration.

5. The method of claim 3, wherein said felid displays a cell-mediated response against said heterologous antigen at about thirty days post administration.

6. The method of claim 3, wherein said antigen is selected from the group consisting of a protozoan parasite antigen, a helminth parasite antigen, an ectoparasite antigen, a fungal antigen, a bacterial antigen, and a viral antigen.

7. The method of claim 3, wherein said antigen is selected from the group consisting of a calicivirus antigen, a coronavirus antigen, a herpesvirus antigen, an immunodeficiency virus antigen, an infectious peritonitis virus antigen, a leukemia virus antigen, a parvovirus antigen, a rabies virus antigen, a Bartonella antigen, a Yersinia antigen, a Dirofilaria antigen, a Toxoplasma antigen, a flea antigen, a flea allergen, a midge antigen, a midge allergen, a mite antigen, a mite allergen, and a tumor antigen.

8. The method of claim 3, wherein said antigen comprises a rabies glycoprotein G antigen.

9. The method of claim 8, wherein said felid displays a protective antibody titer against rabies at about thirty days post administration.

10. The method of claim 3, wherein said recombinant raccoon poxvirus further comprises a nucleic acid molecule encoding an immunomodulator.

11. The method of claim 3, wherein said felid is selected from the group consisting of domestic cats, wild cats and zoo cats.

12. The method of claim 3, wherein said felid is a domestic cat.

13. The method of claim 3, wherein said route comprises an intranasal route.

14. The method of claim 3, wherein said heterologous nucleic acid molecule is positioned in a region of said recombinant raccoon poxvirus selected from the group consisting of an essential gene, a non-essential gene and an intergenic region.

15. The method of claim 3, wherein said recombinant raccoon poxvirus comprises a recombinant raccoon poxvirus genome having a heterologous nucleic acid molecule in a raccoon poxvirus gene selected from the group consisting of a thymidine kinase gene, a hemagglutinin gene, a serpin gene, a cytokine receptor gene, and an interferon receptor gene.

16. The method of claim 3, wherein said heterologous nucleic acid molecule is operatively linked to a transcription control sequence selected from the group consisting of a p11 poxvirus promoter, a p7.5 poxvirus promoter, and a synthetic poxvirus promoter.

17. The method of claim 3, wherein said composition further comprises an excipient.

* * * * *